(12) United States Patent
Chia et al.

(10) Patent No.: US 7,872,143 B2
(45) Date of Patent: *Jan. 18, 2011

(54) FACILE SYNTHESIS OF A SERIES OF LIQUID CRYSTALLINE 2-(4'-ALKOXYPHENYL)-5-CYANOPYRIDINES

(75) Inventors: Win-Long Chia, Sijhih (TW); Yu-Wei Cheng, Hsinchung (TW)

(73) Assignee: Fu Jen Catholic University, Taipei County (TW)

( * ) Notice: Subject to any disclaimer, the term of this patent is extended or adjusted under 35 U.S.C. 154(b) by 834 days.

This patent is subject to a terminal disclaimer.

(21) Appl. No.: 11/760,985

(22) Filed: Jun. 11, 2007

(65) Prior Publication Data

US 2008/0306276 A1  Dec. 11, 2008

(51) Int. Cl.
  *C07D 213/85* (2006.01)
(52) U.S. Cl. .................................................. 546/286
(58) Field of Classification Search ................. 546/286
  See application file for complete search history.

(56) References Cited

U.S. PATENT DOCUMENTS 7,465,802 B2 * 12/2008 Chia et al. .................. 546/286

OTHER PUBLICATIONS

Chia, Win-Long and Yu-Wei Cheng, Novel synthesis and mesophase studies on a series of 2-(4-alkoxyphenyl)-5-cyanopyridines, Sep. 11, 2006, 1-116, Fu Jen Catholic University, Taiwan.

Pavelyuchenko, A. I., N. I. Smimova, T. A. Mikhailova, E. I. Kovshev, and V. V. Titov, Synthesis of 2-(4-alkylphenyl)-and 2-(alkoxphenyl)-5-cyanopyridines and their liquid-crystal characteristics, Nauchno-Issled, Inst. Zhurmal Organicheskoi Khimmi, 1986, 22(5): 1061-5.

* cited by examiner

*Primary Examiner*—Patricia L Morris
(74) *Attorney, Agent, or Firm*—WPAT, P.C.; Anthony King

(57) ABSTRACT

The invention relates to a facile synthesis of a series of 2-(4'-alkoxyphenyl)-5-cyanopyridine liquid crystal compounds which are represented by the following formula (I):

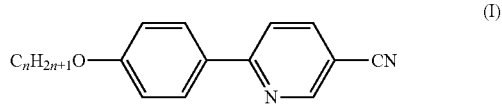

(I)

wherein $C_nH_{2n+1}$ is a linear alkyl group having 2-12 carbon atoms. The synthesis of the liquid crystalline 2-(4'-alkoxyphenyl)-5-cyanopyridine is completed in a two-step reaction. First, a Grignard reagent (such as 4-alkoxyphenylmagnesium bromide) is added to a 3-cyanopyridinium salt (such as N-phenyloxycarbonyl-3-cyanopyridinium chloride) to get a 1,2-dihydropyridine. Then, the 1,2-dihydropyridine is oxidized with o-chloronil to obtain the 2-(4'-alkoxyphenyl)-5-cyanopyridine.

4 Claims, 7 Drawing Sheets

```
Current Date Parameters
NAME                  3CCN0412
EXPNO                        1
PROCNO                       1
F2 - Acquisition Parameters
Date                  20060413
Time                      7.09
INSTRUM                  spect
PROBHD  5mm QNP 1H/1
PULPROG                   zg30
TD                       16384
SOLVENT                  CDC13
NS                          32
DS                           0
SWH               4496.403 Hz
FIDRES            0.274439 Hz
AQ               1.8219508 sec
RG                       406.4
DW                111.200 usec
DE                  6.50 usec
TE                     300.0 K
D1              1.50000000 sec
====  CHANNEL f1 ====
NUC1                        1H
P1                  10.70 usec
PL1                    0.00 dB
SFO1           300.1319508 MHz
F2 - Processing Parameters
SI                       16384
SF             300.1300060 MHz
WDW                         EM
SSB                          0
LB                    0.10 Hz
GB                           0
PC                        1.00
```

FIG.3B

```
Current Date Parameters
NAME                        3CCN0412
EXPNO                              2
PROCNO                             1
F2 - Acquisition Parameters
Date                        20060413
Time                            7.16
INSTRUM                        spect
PROBHD   5mm QNP 1H/1
PULPROG                       zgpg30
TD                             65536
SOLVENT                        CDCl3
NS                               621
DS                                 0
SWH                    18832.393 Hz
FIDRES                   0.287360 Hz
AQ                       1.7400306 se
RG                              4096
DW                          26.550 us
DE                           6.50 us
TE                           300.0 K
D1                      1.20000005 se
d11                     0.03000000 se
d12                     0.00002000 se
        ==== CHANNEL f1 ====
NUC1                             13C
P1                           9.50 us
PL1                          0.00 dB
SFO1                   75.4763978 MH
        ==== CHANNEL f2 ===
CPDPRG2                      waltz16
NUC2                              1H
PCPD2                       90.00 us
PL2                         -2.00 dB
PL12                        18.50 dB
PL13                        21.50 dB
SFO2                  300.1313506 MH
F2 - Processing Parameters
SI                             32768
SF                     75.4677439 MH
WDW                               EM
SSB                                0
LB                           3.00 Hz
GB                                 0
PC                              1.00
```

*FIG.4B*

FACILE SYNTHESIS OF A SERIES OF LIQUID CRYSTALLINE 2-(4'-ALKOXYPHENYL)-5-CYANOPYRIDINES

BACKGROUND OF THE INVENTION

1. Field of the Invention

The present invention relates to a facile synthetic method of a series of 2-(4'-alkoxyphenyl)-5-cyanopyridine liquid crystal compounds, and more particularly to a synthetic method which uses the Grignard reagent and promotes electrophilic properties of pyridines in the synthesis.

2. Description of the Prior Art

With the rapid development of internet, communication and computer manufacturing technologies, a variety of portable electronic products such as cellular phones, mobile computers, personal digital assistants (PDA), palm audio/visual players (e.g. MP3 and MP4 players), and the like, are playing an indispensable role in modern life. As the present electronics moves in a trend of thinner products, liquid crystal displays have been gradually taking the place of conventional cathode ray tubes. Because of their advantages in thin structure, light weight, low power consumption, low radiation contamination, and compatibility with semiconductor processing technology, liquid crystal displays have found broad applications in diverse electronic products. In order to advance liquid crystal manufacturing technology, it is essential to further improve and develop liquid crystal materials.

Because of its advantages in high response speed, high resolution, and wide viewing angle, the Highly Sensitive Electric Field Induced Liquid Crystal has become a common optical switching material used in the new generation of liquid crystal displays. Among the Highly Sensitive Electric Field Induced Liquid Crystals, 2-(4'-alkoxyphenyl)-5-cyanopyridine liquid crystal compounds are similar in molecular structure to heptyloxycyanobiphenyl (7OCB), which has been widely used in commerce. Therefore, the former has a great potential to be used as molecular optical switches in liquid crystal displays.

Conventional synthesis of 2-(4'-alkoxyphenyl)-5-cyanopyridine was disclosed by Pavelyuchenko, A. I. et al. in 1986 (Pavelyuchenko, A. I., T. A. Mikhailova, E. I. Kovshev, V. V. Titov, Nauchno-lssled, Inst. *Zhurmal Organicheskoi Khimmi*, 1986, 22(5): 1061-5). As shown in FIG. 1, the conventional synthesis of 2-(4'-alkoxyphenyl)-5-cyanopyridine includes the following steps:

1. Sodium benzoylacetaldehydide (14) was obtained by the condensation of alkoxyacetophenones (11) with ethyl formate ($HCO_2C_2H_5$) (12) and sodium (13) in ether and gave yields of 70-76%.
2. Arylcyanopyridine (16) was obtained by the cyclization of sodium benzoylacetaldehyde (14) with cyanoacetamide ($CNCH_2CONH_2$)(15) in a water-dioxane mixture. The yield of the arylcyanopyridine (16) amounted to 60-65% with a water-dioxane ratio of 1:10.
3. The substitution of the oxygen of the carbonyl group by a chlorine atom in arylcyanopyridine (16) was taken place on heating with phenylphosphonyl chloride (Ph-$POCl_2$)(17), and the yields of 6-(4'-alkoxyphenyl)-2-chloro-3-cyanopyridines (18) amounted to 70-80%.
4. The chlorine of the carbonyl group in 6-(4'-alkoxyphenyl)-2-chloro-3-cyanopyridines (18) were reduced by catalytic hydrogenation over 10% Palladium/Carbon (Pd/C)(19), and the yields of the obtained 2-(4'-alkoxyphenyl)-5-cyanopyridine (I) amounted to 39-60%. Then, the synthesis of 2-(4'-alkoxyphenyl)-5-cyanopyridine (I) was completed after the purification of the obtained 2-(4'-alkoxyphenyl)-5-cyanopyridine (I).

The four-step synthetic method mentioned above involves many procedures and consumes a large amount of reagents; moreover, some of the reagents are costly, especially the rare element palladium used in the fourth step. Worst of all, the total yield is only 8.5-13.4%. For these reasons, the method is not suitable for industrial production.

Accordingly, there are still many disadvantages in the conventional synthesis of 2-(4'-alkoxyphenyl)-5-cyanopyridine liquid crystal compounds, and it needs to be improved.

The inventor, in view of the drawbacks of the conventional synthetic method of 2-(4'-alkoxyphenyl)-5-cyanopyridine liquid crystal compounds, after many years of R&D on innovative improvement, has successfully developed a facile synthetic method of a series of 2-(4'-alkoxyphenyl)-5-cyanopyridine liquid crystal compounds.

SUMMARY OF THE INVENTION

The present invention provides a facile synthetic method of a series of 2-(4'-alkoxyphenyl)-5-cyanopyridine liquid crystal compounds, which method can complete the synthesis of 2-(4'-alkoxyphenyl)-5-cyanopyridine liquid crystal compounds in only two steps.

The present invention also provides a facile synthetic method of a series of 2-(4'-alkoxyphenyl)-5-cyanopyridine liquid crystal compounds with fewer procedures and increased yield when compared to the conventional synthetic method.

Referring to FIG. 2, the synthesis of a series of 2-(4'-alkoxyphenyl)-5-cyanopyridine liquid crystal compounds is achieved by way of forming pyridinium salt (22) to promote electrophilic properties of pyridine, and combining a Grignard reagent (a relatively hard base with chemical formula of RMgX, wherein X is a halogen and R is an alkylaryl group) (21) with a regioselectively attacking property, i.e., the product of Grignard reagent attacking on the cyano group was not found and on the other sites of the pyridine ring in the presence of pyridinium salt was found too little to be isolated. First, a 1,2-dihydropyridine intermediate (23) is formed, and then the 1,2-dihydropyridine intermediate (23) is oxidized to obtain the resulting liquid crystal compound (I) of 2-(4'-alkoxyphenyl)-5-cyanopyridine. This method not only can be completed in two steps but also has a higher throughput (yield 72-83%).

Namely, a facile synthetic method of a series of liquid crystalline 2-(4'-alkoxyphenyl)-5-cyanopyridine of the present invention relates to synthesis of the compounds represented by the following formula (I):

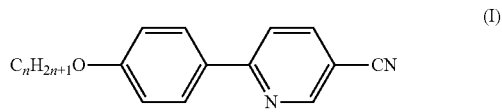

(I)

wherein $C_nH_{2n+1}$ is a linear alkyl, n=2~12.

The method comprises the following steps:

Step 1 React a Grignard reagent with 3-cyanopyridinium salt (such as N-phenyloxycarbonyl-3-cyanopyridinium chloride) in a nucleophilic reaction to obtain a 1,2-dihydropyridine intermediate;

Step 2 Oxidize the 1,2-dihydropyridine intermediate with an oxidant to obtain 2-(4'-alkoxyphenyl)-5-cyanopyridine liquid crystal compounds, wherein the Grignard reagent is produced by adding magnesium to 4-alkoxybromobenzene;

the 3-cyanopyridinium salt is formed by adding phenyl chloroformate to 3-cyanopyridine; and said oxidant is o-chloronil.

These features and advantages of the present invention will be fully understood and appreciated from the following detailed description of the preferred embodiment with reference to the accompanying Drawings.

BRIEF DESCRIPTION OF THE DRAWINGS

FIG. 3B is the current date parameters corresponding to FIG. 3A;

FIG. 4B is the current date parameters corresponding to FIG. 4A; and

DETAILED DESCRIPTION OF THE PREFERRED EMBODIMENT

EXAMPLE 1

A Facile Synthesis of a Series of 2-(4'-alkoxyphenyl)-5-cyanopyridine Liquid Crystal and its Product Analysis I. Facile Synthesis of 2-(4'-alkoxyphenyl)-5-cyanopyridine Liquid Crystal Add 12 millimole of dry magnesium particles to 20 ml of tetrahydrofuran (THF) solution containing 10 millimole of 4-butoxybromobenzene in inert gas to form a Grignard reagent of 4-butoxyphenylmagnesium bromides, then gradually add the Grignard reagent to 20 ml of tetrahydrofuran (THF) solution containing 10 millimole of N-phenyloxycarbonyl-3-cyanopyridinium chloride under low temperature (−20° C.), allow the mixed solution to gradually return to ambient temperature, stir the mixed solution for 8 hours, remove the tetrahydrofuran (THF), extract the remainder with ether, rinse it twice with 10% hydrochloric acid and once with saturated saline, then dry it with magnesium sulfate to obtain 1,2-dihydropyridine intermediate. (The yield rate of the intermediate is about 95%).

Dissolve the 1,2-dihydropyridine intermediate in 20 ml dry toluene, add about 1.5 equivalent of o-chloronil to the 1,2-dihydropyridine intermediate to oxydize it, then heat the resultant solution in inert gas for a few hours under reflux, quench it with 25 ml of 1N sodium hydroxide (NaOH) solution, extract with ether, then after filtering and usual aqueous phase post-treatment and separation with column chromatography, 2-(4'-butoxyphenyl)-5-cyanopyridine liquid crystal compounds of formula (I) can be obtained (the total yield is 83%).

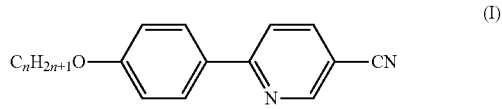

wherein $C_nH_{2n+1}$ is a linear alkyl, n=4.

Furthermore, THF solution containing alkoxybromobenzene with different carbon number, for example 4-propoxybromobenzene, 4-pentoxybromobenzene, 4-hexoxybromobenzene, or 4-heptoxybromobenzene, is used to form a Grignard reagent of 4-alkoxyphenylmagnesium bromides with different carbon number, i.e. 4-propoxyphenylmagnesium bromides, 4-pentoxyphenylmagnesium bromides, 4-hexoxyphenylmagnesium bromides, or 4-heptoxyphenylmagnesium bromides, by following the method mentioned above. Then, 2-(4'-propoxyphenyl)-5-cyanopyridine (n=3), 2-(4'-pentoxyphenyl)-5-cyanopyridine (n=5), 2-(4'-hexoxyphenyl)-5-cyanopyridine (n=6), or 2-(4'-heptoxyphenyl)-5-cyanopyridine (n=7) liquid crystal compounds of formula (I) is obtained also by following the method mentioned above. As shown in Table 1, the total yield of 2-(4'-alkoxyphenyl)-5-cyanopyridine liquid crystal compounds through above two-step method is 72-83%, depending on the carbon number of the linear alkyl group.

TABLE 1

The yield of 2-(4'-alkoxyphenyl)-5-cyanopyridine liquid crystal compounds for the synthetic method of the present invention

| N (carbon number of linear alkyl) | Yield (%) |
|---|---|
| 3 | 80 |
| 4 | 83 |
| 5 | 78 |
| 6 | 72 |
| 7 | 76 |

II. Product Analysis

Figure 1:
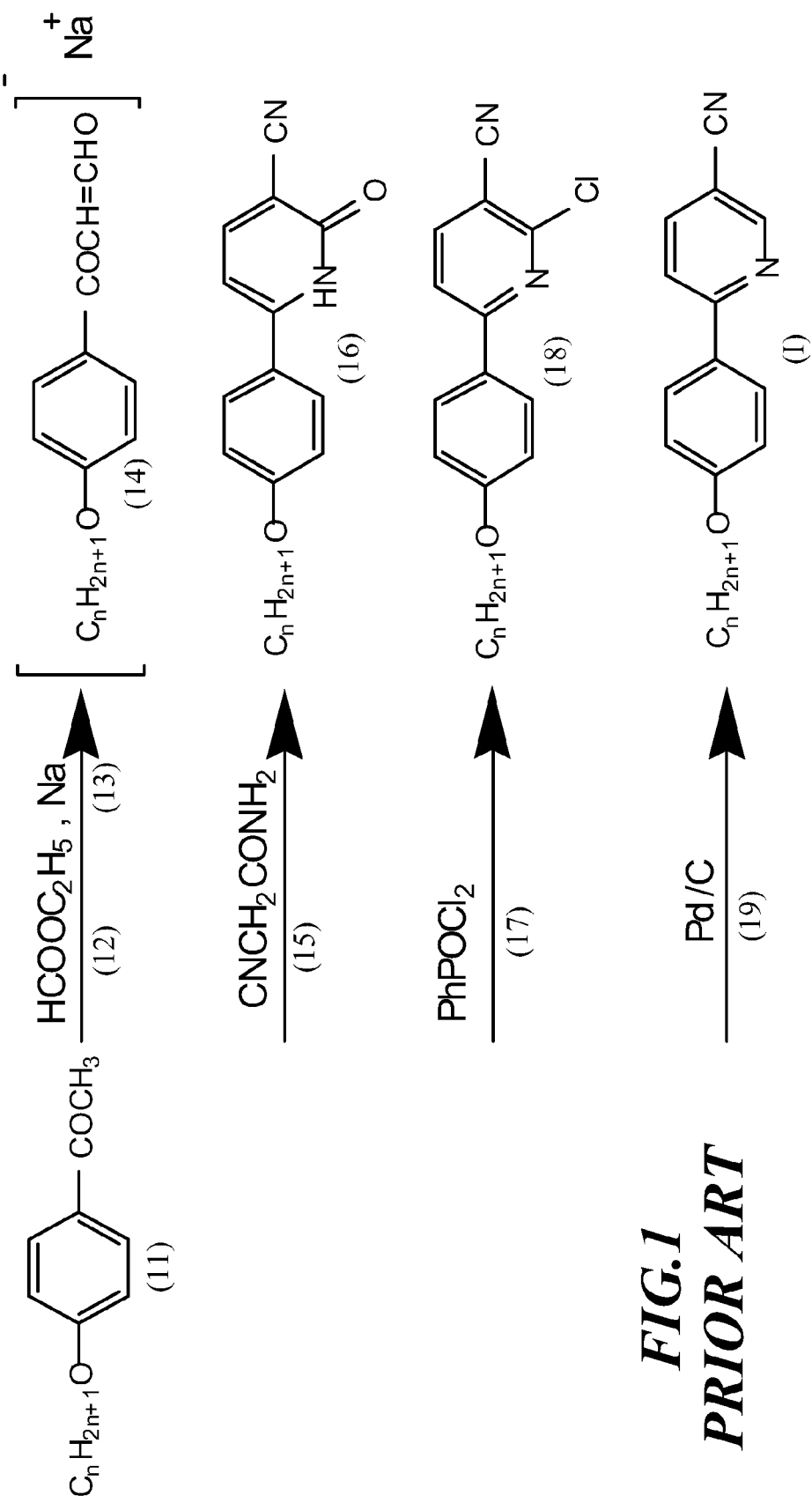
FIG. 1 shows the conventional synthetic method of 2-(4'-alkoxyphenyl)-5-cyanopyridine liquid crystal compounds.
Figure 2:
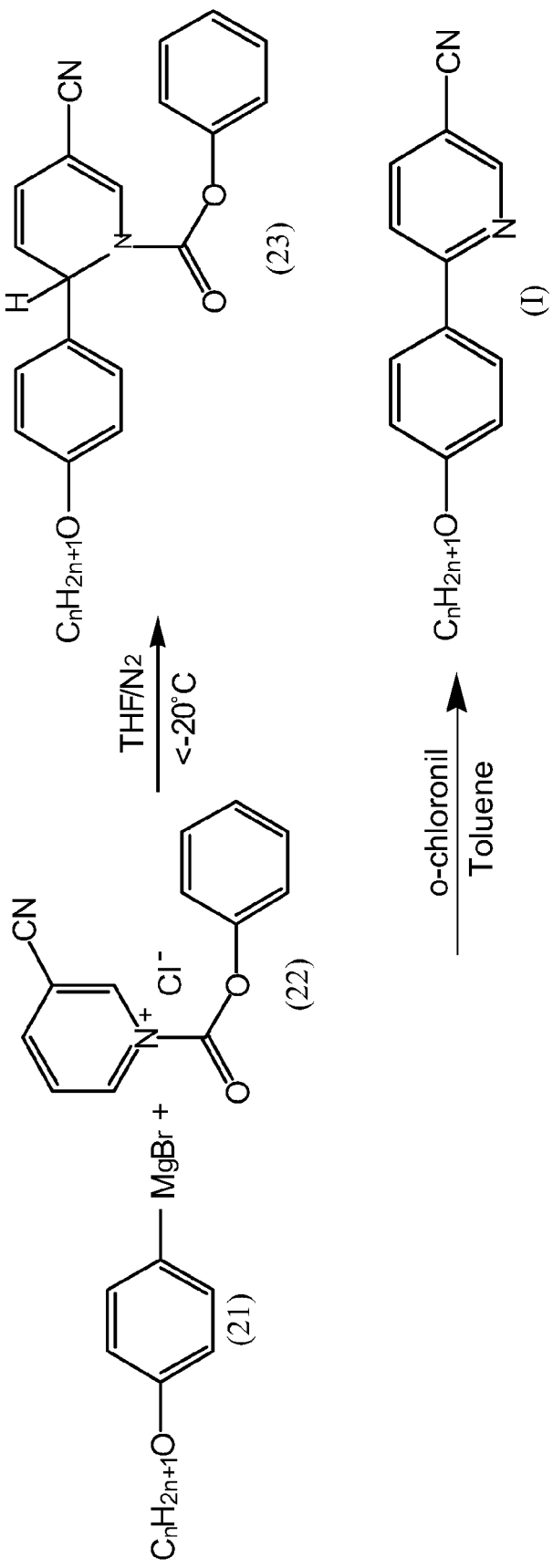
FIG. 2 shows a facile synthetic method of a series of 2-(4'-alkoxyphenyl)-5-cyanopyridine liquid crystal compounds of the present invention.
Figure 3A:
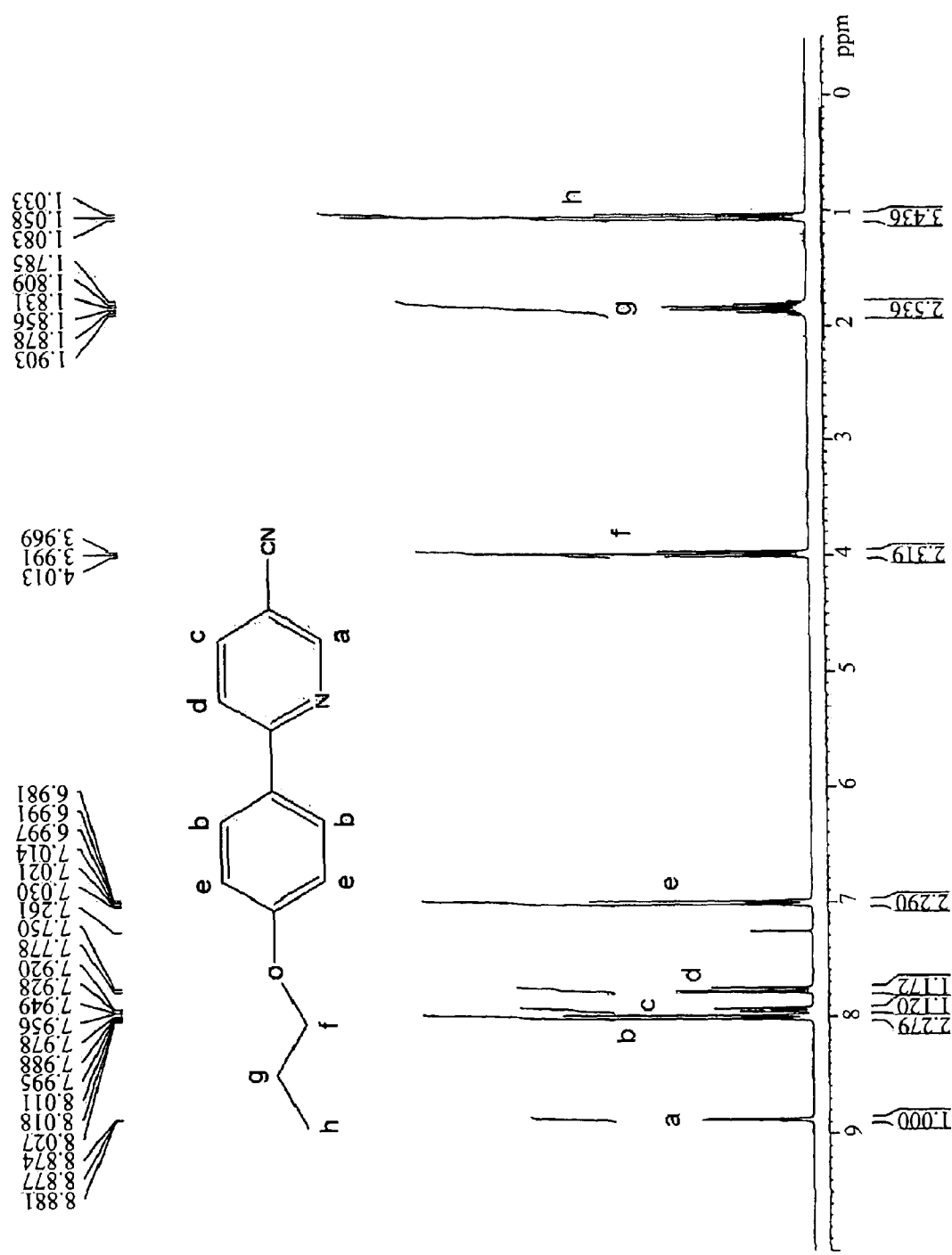
FIG. 3A is a proton magnetic resonance spectrum of 2-(4'-propoxyphenyl)-5-cyanopyridine (n=3) liquid crystal compounds made by the synthetic method of the present invention.
Figure 4A:
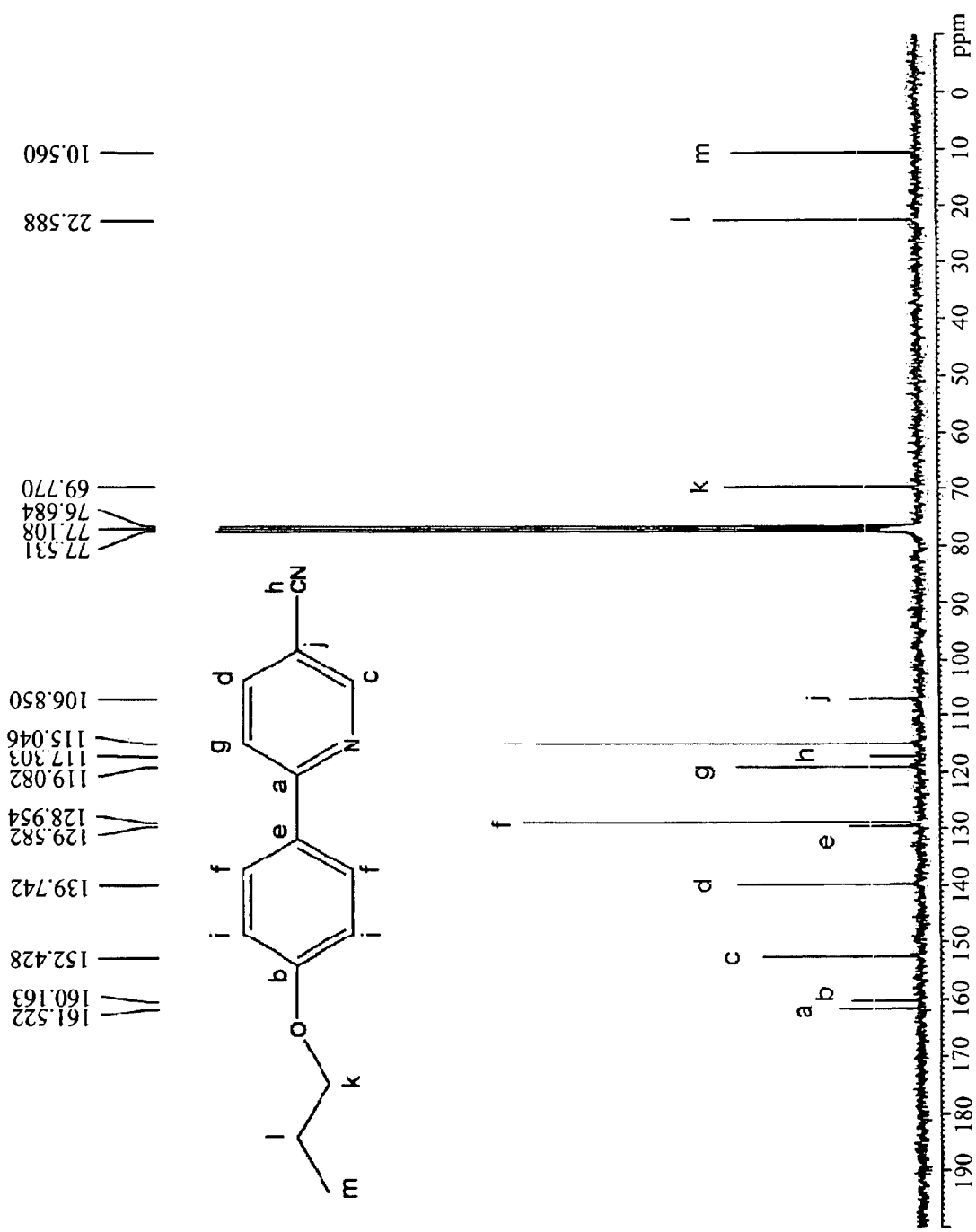
FIG. 4A is a carbon magnetic resonance spectrum of 2-(4'-propoxyphenyl)-5-cyanopyridine (n=3) liquid crystal compounds made by the synthetic method of the present invention.

1. Analysis of 2-(4'-alkoxyphenyl)-5-cyanopyridine Liquid Crystal Compounds with Magnetic Resonance Spectrum Purify the 2-(4'-alkoxyphenyl)-5-cyanopyridine liquid crystal compounds synthesized by the facile synthetic method mentioned above. First, separate the by-products of the 2-(4'-alkoxyphenyl)-5-cyanopyridine liquid crystal compounds with column chromatography (the solvent used in the column chromatography is a solvent of dichloromethane ($CH_2Cl_2$):hexane=2:1). Then, re-crystallize the 2-(4'-alkoxyphenyl)-5-cyanopyridine liquid crystal compounds several times with ethyl ether under low temperature (about 5° C.) to remove impurities and obtain pure liquid crystal compounds. After washing the pure liquid crystal compounds with hexane, the structures of the re-crystallized products are analyzed with magnetic resonance spectroscopy. The structure of 2-(4'-propoxyphenyl)-5-cyanopyridine (n=3) liquid crystal compound, for example, is shown in FIGS. 3A/3B and FIGS. 4A/4B, wherein FIG. 3A is the proton magnetic resonance spectrum of the liquid crystal compound with the corresponding current date parameters shown in FIG. 3B, and FIG. 4A is its carbon magnetic resonance spectrum with the corresponding current date parameters shown in FIG. 4B. It can be confirmed from FIG. 3A and FIG. 4A that the structure of the 2-(4'-propoxyphenyl)-5-cyanopyridine liquid crystal compound synthesized by the method of the present invention is correct.

Figure 5:
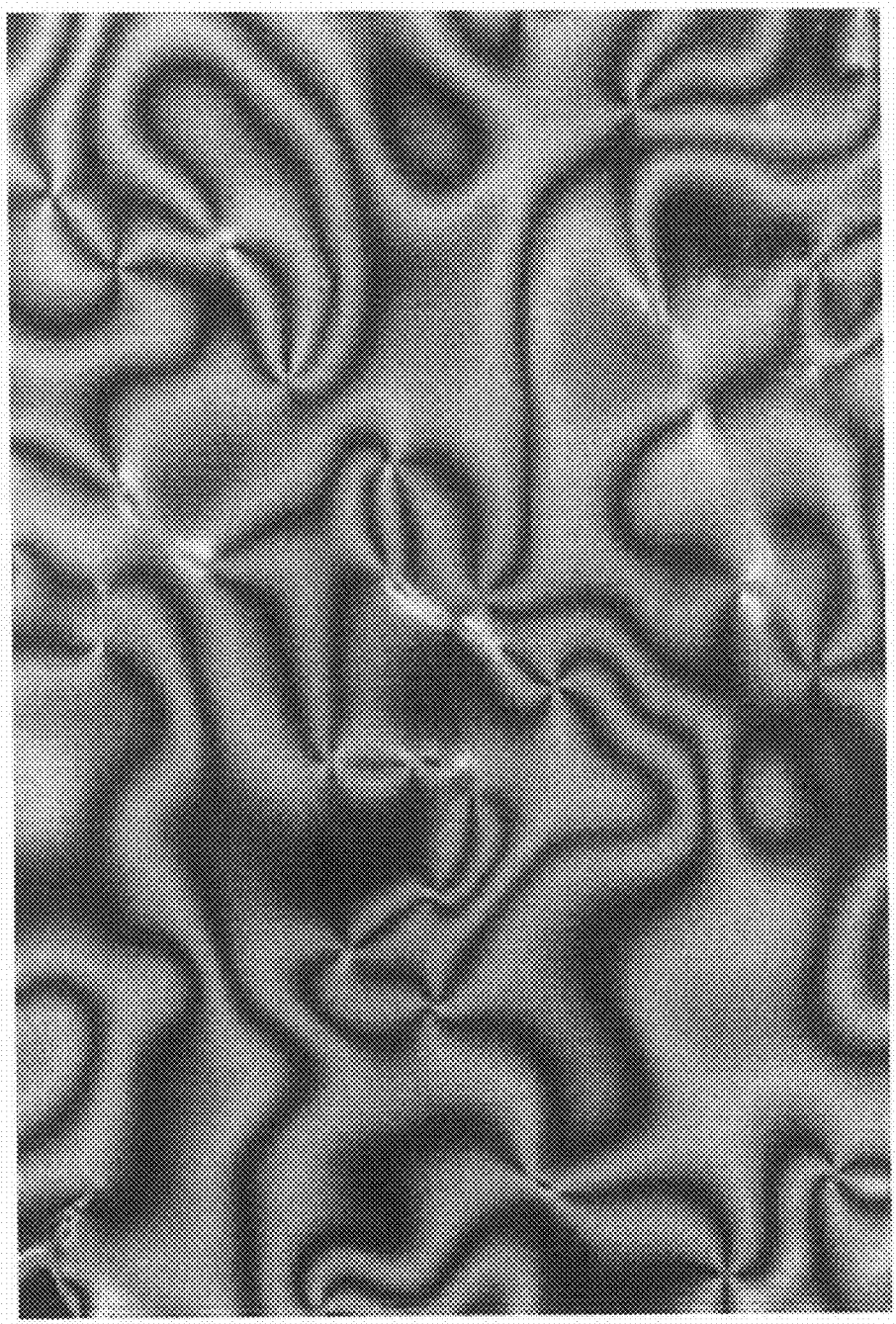
FIG. 5 shows that 2-(4'-propoxyphenyl)-5-cyanopyridine (n=3) liquid crystal compound represents ribbon texture when the compound has been heated from crystal to nematic phase (97° C.), as viewed under 100× polarizing optical microscope.

2. Observed Temperature Variance of 2-(4'-alkoxyphenyl)-5-cyanopyridine Liquid Crystal Phase The liquid crystal phase of 2-(4'-alkoxyphenyl)-5-cyanopyridine was observed under different temperatures. The result is shown in Table 2, wherein Cr represents crystal phase, N represents nematic phase, S represents smectic phase, and I represents isotropic phase (i.e. the liquid crystal compound is in liquid phase). As shown in Table 2, the 2-(4'-alkoxyphenyl)-5-cyanopyridine liquid crystal compounds synthesized by the method of the present invention have excellent variances of liquid crystal phase under different temperatures. For example, as shown in FIG. 5, 2-(4'-propoxyphenyl)-5-cyanopyridine liquid crystal compound (n=3) represents ribbon texture when the compound has been heated from crystal to nematic phase (97° C.), as viewed under 100× polarizing optical microscope.

TABLE 2

Phase transition of 2-(4'-alkoxyphenyl)-5-cyanopyridine liquid crystal compounds

| n (carbon number of linear alkyl) | Temperature Variance of Liquid Crystal Phase | | | | | |
|---|---|---|---|---|---|---|
| 3 | Cr | 93.6° C. → / ← 76.1° C. | N | 97.2° C. → / ← 95.6° C. | I | |
| 4 | Cr | 91.6° C. → / ← 64.9° C. | N | 102.9° C. → / ← 101.3° C. | I | |
| 5 | Cr | 59.2° C. → / ← 35.9° C. | N | 95.4° C. → / ← 93.8° C. | I | |
| 6 | Cr | 62.4° C. → / ← 32.7° C. | N | 99.4° C. → / ← 97.8° C. | I | |
| 7 | Cr | 58.4° C. → / ← 43.2° C. | S | 88.6° C. → / ← 87.0° C. | N | 97.4° C. → / ← 95.6° C. | I |

3. Elemental Analysis of 2-(4'-alkoxyphenyl)-5-cyanopyridine Liquid Crystal Compounds Elemental analysis was performed on the re-crystallized 2-(4'-alkoxyphenyl)-5-cyanopyridine liquid crystal compounds mentioned above, and the result is shown in Table 3. It can be seen from Table 3 that the analytic values of the elements of the 2-(4'-alkoxyphenyl)-5-cyanopyridine liquid crystal compounds synthesized by the method of the present invention are close to the theoretical values; therefore, the 2-(4'-alkoxyphenyl)-5-cyanopyridine liquid crystal compounds synthesized by the present method are of high purity.

TABLE 3

Elemental analysis of 2-(4'-alkoxyphenyl)-5-cyanopyridine liquid crystal compounds

| n (carbon number of linear alkyl) | Elemental Analysis |
|---|---|
| 3 | Theoretical value: C, 75.61%; H, 5.92%; N, 11.76% Analytic value: C, 75.63%; H, 5.93%; N, 11.74% |
| 4 | Theoretical value: C, 76.16%; H, 6.39%; N, 11.10% Analytic value: C, 76.12%; H, 6.44%; N, 11.09% |
| 5 | Theoretical value: C, 76.66%; H, 6.81%; N, 10.52% Analytic value: C, 76.68%; H, 6.83%; N, 10.52% |
| 6 | Theoretical value: C, 77.11%; H, 7.19%; N, 9.99% Analytic value: C, 77.07%; H, 7.20%; N, 9.98% |
| 7 | Theoretical value: C, 77.52%; H, 7.53%; N, 9.52% Analytic value: C, 77.40%; H, 7.55%; N, 9.48% |

A facile synthetic method of a series of 2-(4'-alkoxyphenyl)-5-cyanopyridine liquid crystals provided by the present invention has the following advantages when compared to the method cited above and other conventional techniques:

1. There are only two steps in the present method to complete the synthesis of 2-(4'-alkoxyphenyl)-5-cyanopyridine liquid crystal compounds. The present method has two fewer steps than the conventional method, which means a large amount of saving in cost and labor on commercial scale; therefore, the present method has a greater potential in industrial utilization than the conventional methods have.

2. The total yield of 2-(4'-alkoxyphenyl)-5-cyanopyridine liquid crystal compounds synthesized by the present method is much higher than the compounds synthesized by the conventional method; therefore, the present method not only has a higher production efficiency but also saves a large amount of money on commercial scale production.

3. Rare elements such as palladium are not used in the present method; consequently, the cost of the present method is much less then the cost of the conventional method.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A facile synthetic method for synthesizing a series of 2-(4'-alkoxyphenyl)-5-cyanopyridine liquid crystal compounds having the following formula (I),

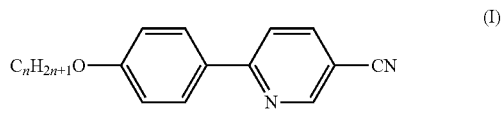

(I)

wherein $C_nH_{2n+1}$ is a linear alkyl group, n=2~12, the synthetic method comprising the following steps:
(1) reacting a Grignard reagent with N-phenyloxycarbonyl-3-cyanopyridinium chloride in a nucleophilic reaction to obtain a 1,2-dihydropyridine intermediate; and
(2) oxidizing the 1,2-dihydropyridine intermediate with an oxidant to obtain 2-(4'-alkoxyphenyl)-5-cyanopyridine liquid crystal compounds.

2. The facile synthetic method for synthesizing a series of 2-(4'-alkoxyphenyl)-5-cyanopyridine liquid crystal compounds of claim 1, wherein the Grignard reagent is produced by adding magnesium to 4-alkoxybromobenzene.

3. The facile synthetic method for synthesizing a series of 2-(4'-alkoxyphenyl)-5-cyanopyridine liquid crystal compounds of claim 1, wherein the N-phenyloxycarbonyl-3-cyanopyridinium chloride is formed by adding phenyl chloroformate to 3-cyanopyridine.

4. The facile synthetic method for synthesizing a series of 2-(4'-alkoxyphenyl)-5-cyanopyridine liquid crystal compounds of claim 1, wherein the oxidant is o-chloronil.

\* \* \* \* \*